United States Patent
Slonneger

(10) Patent No.: US 9,329,694 B2
(45) Date of Patent: May 3, 2016

(54) PREEMPTIVE MACHINE LEARNING-BASED GESTURE RECOGNITION

(71) Applicant: MOTOROLA MOBILITY LLC, Chicago, IL (US)

(72) Inventor: Andrew M. Slonneger, Crystal Lake, IL (US)

(73) Assignee: Google Technology Holdings LLC, Mountain View, CA (US)

( * ) Notice: Subject to any disclaimer, the term of this patent is extended or adjusted under 35 U.S.C. 154(b) by 0 days.

(21) Appl. No.: 14/454,069

(22) Filed: Aug. 7, 2014

(65) Prior Publication Data

US 2015/0355718 A1    Dec. 10, 2015

Related U.S. Application Data

(60) Provisional application No. 62/008,589, filed on Jun. 6, 2014.

(51) Int. Cl.
*G06F 3/01* (2006.01)
*A61B 5/00* (2006.01)
*G06N 7/02* (2006.01)

(52) U.S. Cl.
CPC ............. *G06F 3/017* (2013.01); *A61B 5/681* (2013.01); *G06F 3/014* (2013.01); *G06N 7/023* (2013.01)

(58) Field of Classification Search
CPC .................................................... G06F 3/017
See application file for complete search history.

(56) References Cited

U.S. PATENT DOCUMENTS

| | | | |
|---|---|---|---|
| 2010/0162215 A1 | 6/2010 | Purcell et al. | |
| 2013/0191741 A1* | 7/2013 | Dickinson | G06F 1/163 715/702 |
| 2014/0347491 A1* | 11/2014 | Connor | A61B 5/1114 348/158 |

* cited by examiner

*Primary Examiner* — Gerald Johnson
(74) *Attorney, Agent, or Firm* — Shumaker & Sieffert, P.A.

(57) ABSTRACT

A system and method for detecting a viewing gesture with respect to a wrist-worn device employ a logistic-regression model to pre-learn gesture metrics for on events. An output model is produced for deployment on a consumer device, allowing real-time gesture detection with high accuracy and low latency.

29 Claims, 4 Drawing Sheets

PREEMPTIVE MACHINE LEARNING-BASED GESTURE RECOGNITION

RELATED APPLICATION

This application claims priority to U.S. Provisional Patent Application 62/008,589, filed on Jun. 6, 2014, which is incorporated herein by reference in its entirety.

TECHNICAL FIELD

The present disclosure is related generally to human device interactions and, more specifically, to a system and method for deploying machine pre-learning in real-time error-intolerant environments.

BACKGROUND

Our lives become slightly easier each day as more and more minor tasks are delegated to smart electronic devices. Such devices can manage our schedules and communications, help maintain our health, and do many more things that are so simple that we now take them for granted. But one thing that all such devices have in common is their need for a source of electrical power to support their operation. Most often, such devices are mobile, and consequently, the most common power sources are also mobile. Of these, batteries tend to predominate at the moment.

Whatever the mobile power source may be, its inherently limited nature makes it desirable to avoid power waste when using such devices. Thus for example, devices that support wireless communications may retire to a sleep mode when communications are infrequent, and device processors may go into a low-power idle mode after some period of inactivity in order to save power. Nonetheless, some device features are always on due to the difficulty in knowing when they should be turned off. For example, a device screen may be turned on or off by a user, but would not necessarily otherwise know to turn itself off, because it would not know when the user desires to see the screen and when the user does not.

Since the display of a device is often responsible for a significant portion of the total power consumed by the device, the lack of automated control over power usage with respect to perpetually on but infrequently viewed devices can significantly impact battery life. While certain embodiments of the disclosed principles lend themselves to mitigating such issues, no particular solution of any particular problem should be seen as a requirement of any claim unless expressly stated otherwise. Moreover, this Background section is provided as an introduction to the reader unfamiliar with the subject matter, and is not intended to comprehensively or precisely describe known prior art. As such, this section is disclaimed as, and is not to be taken as, prior art, a description of prior art, or the thoughts of anyone other than the inventors themselves.

BRIEF DESCRIPTION OF THE SEVERAL VIEWS OF THE DRAWINGS

While the appended claims set forth the features of the present techniques with particularity, these techniques, together with their objects and advantages, may be best understood from the following detailed description taken in conjunction with the accompanying drawings of which:

DETAILED DESCRIPTION

Figure 1:
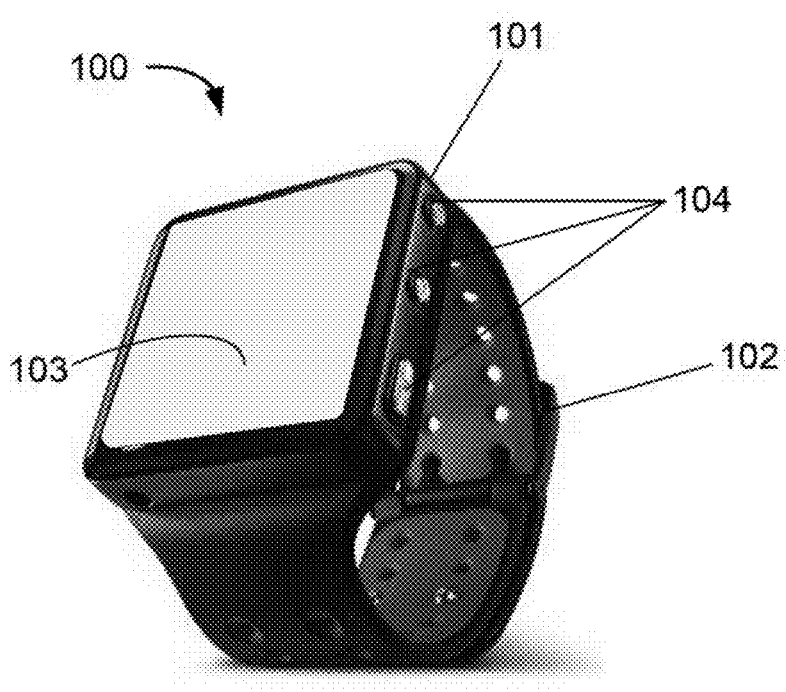
FIG. 1 illustrates an example mobile electronic device within which embodiments of the disclosed principles may be implemented.
Figure 2:
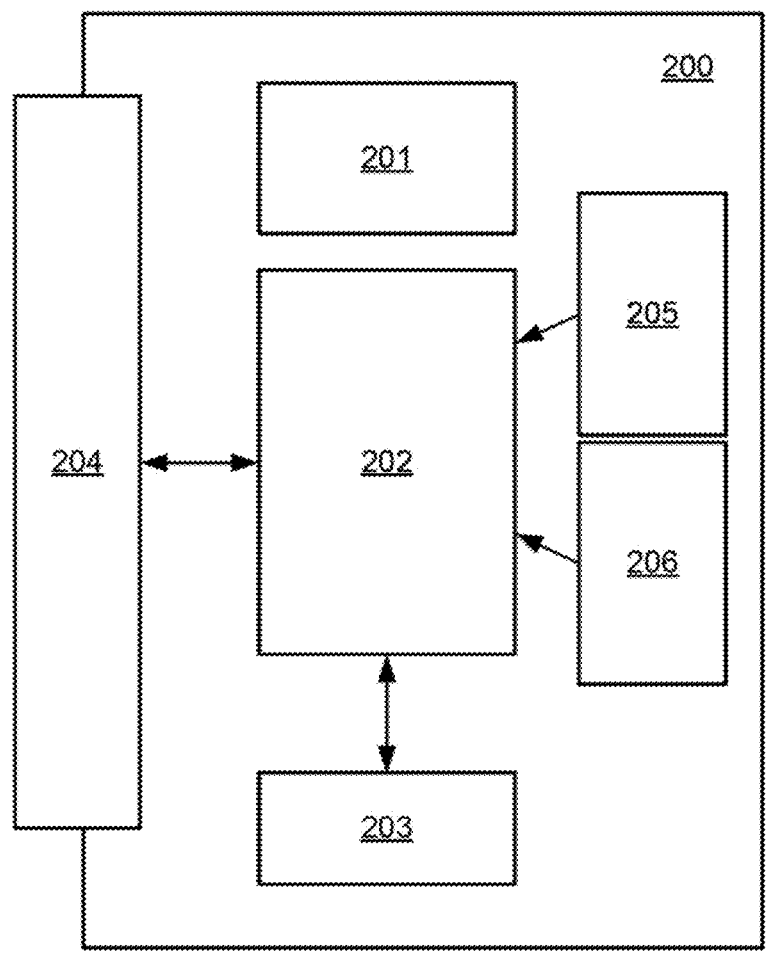
FIG. 2 is a simplified architectural view of the mobile electronic device of FIG. 1.

Before discussing details and examples of the disclosed principles, an example environment is discussed in order to aid the reader in understanding the remainder of the discussion. In this connection, FIG. 1 is a perspective drawing of an exemplary mobile wearable device within which embodiments of the disclosed principles may be implemented. In particular, the illustrated device 100 is a wearable watch having extended functionality beyond keeping time. The illustrated watch 100 includes a case 101 containing hardware components including electronic components for structural and functional operation of the watch 100. The electronic components are described in greater detail with respect to FIG. 2.

The illustrated watch 100 also includes a band or strap 102, usable to affix the watch 100 to a user's wrist or forearm. In this way, the user may turn his wrist to view a face or display 103 of the watch 100 periodically. As suggested above, while a watch is used for telling time in a traditional sense of the word, the illustrated device 100 is a computerized device having many functions. While one of these functions may be to keep and display the time of day, other functions may include location services, e.g., via the Global Positioning System, communication services (e.g., via cellular or other wireless facilities), vital-sign detection and recording, stride detection and recording, and so on.

In an embodiment, the watch 100 may also include hardware user-interface controls 104. These can include, for example, power controls, display-mode controls, communication controls, privacy controls, and so on. As noted above, the watch case 101 contains a number of structural and electronic components that support the use and functioning of the watch. A simplified electronic architecture of the internal electronic components is shown by way of example in FIG. 2. In the illustrated arrangement 200, the watch contains a power source 201, which may be, as discussed, a battery, fuel cell, or other source of electrical power for the remaining electrical components. Also included in the illustrated architecture is a processor 202, which may be a stand-alone microprocessor or an embedded processor within a controller, microcontroller, or other computerized component or module.

The processor 202 operates by executing computer-executable instructions that are electronically read from a non-transitory computer-readable medium 203. The medium 203 may be any suitable volatile or nonvolatile medium or combination of multiple such media. The processor 202 receives inputs from a device display 204 which is a touch-screen display in the illustrated embodiment, from one or more sensors including a three-dimensional ("3D") accelerometer 205, and optionally from hardware user controls 206.

In an embodiment of the disclosed principles, the accelerometer 205 is used by the processor 202 to determine when the user has executed a gesture indicating that the watch display 204 is to be powered on in order to be easily visible to the user. Otherwise the processor 202 maintains the watch display 204 in a powered-off or low-power state.

The movement ordinarily made by a user to view a watch on his wrist can be ambiguous; the gesture is so simple that distinguishing it from other similar gestures is difficult. A person watching another person might accurately judge such a gesture based on his life experience. However, with respect to machine recognition of the gesture, the extended training time required and the inconvenience to the user during such training is generally prohibitive of a machine-learning approach to this problem. However, in an embodiment of the disclosed principles, a machine pre-learning method is employed to provide real-time gesture recognition at a later time in this error-intolerant environment.

In particular, a logistic-regression model is provided a priori, that is, not in real time with respect to the end user, but beforehand. The model is implemented on a device, and accelerometer data are collected with multiple users throughout the day. Each user marks times when the display is desired to turn on. Such events are referred to herein as positive events. Similar events that the user does not mark are used as negative events for training purposes. Numerous metrics are calculated using a history of accelerometer data surrounding, but mostly prior, to each event, since the goal is prediction of the event. These metrics are then employed as features for logistic regression. At this point, the logistic-regression model is trained, validated and tested offline, e.g., via MATLAB™ or another suitable environment. The output model that is produced includes a vector of metric means, a vector of metric standard deviations, and a vector of metric weights.

Figure 3:
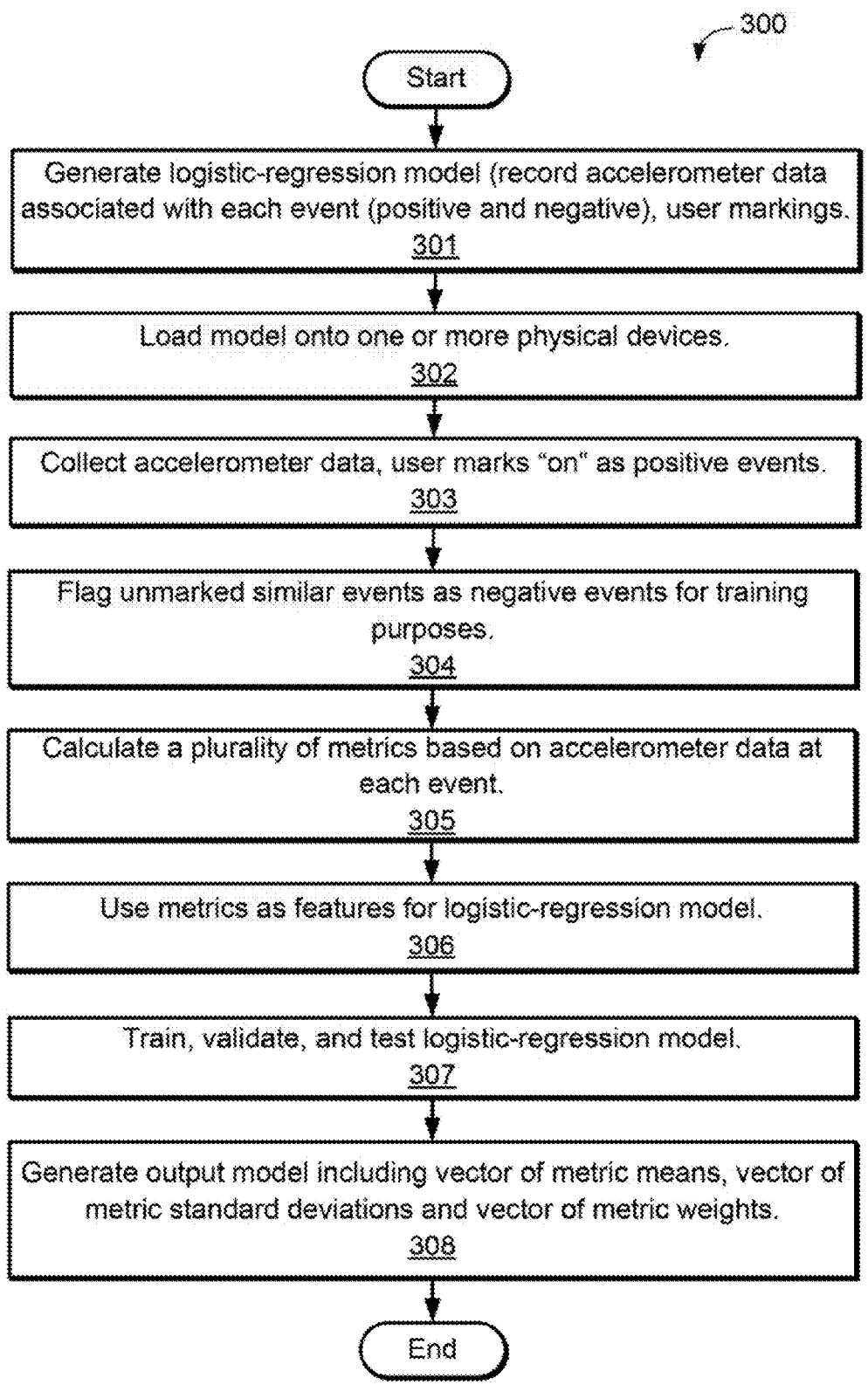
FIG. 3 is a flowchart illustrating a process for generating a logistic-regression output model of an embodiment of the disclosed principles.

FIG. 3 provides a flowchart showing a process 300 of employing the machine pre-learning technique described above. At stage 301 of the process 300, the logistic-regression model is generated, e.g., including recording accelerometer data associated with each event (positive and negative) and the user markings. The model is loaded onto one or more physical devices at stage 302, each physical device being wearable by a user and having at least a 3D accelerometer and a selection or "power on" button or interface element.

At stage 303, each device is worn by a user, and accelerometer data are collected throughout the day, e.g., at a 10 Hz or other sampling frequency. Each user employs the selection or power on button to signify "on" times when the display was desired to turn on, that is, when the user made a gesture to bring the device display into view. Such events are referred to herein as positive events. Similar events that the user did not mark are flagged at stage 304 for use as negative events for training purposes.

At stage 305, a plurality of metrics are calculated based on accelerometer data surrounding each event. The selection of samples may be biased, perhaps heavily so, towards samples prior to the event, since the goal is prediction of the event. These metrics are then employed as features for logistic regression at stage 306. At this point, the logistic-regression model is trained, validated, and tested offline at stage 307, e.g., via MATLAB™ or another suitable environment. The output model that is produced at stage 308 includes a vector of metric means, a vector of metric standard deviations, and a vector of metric weights.

On a prototype device, the following functionality was implemented and performed in real-time:
tracking of accelerometer history;
detection of events;
production of metrics;
production of a final metric for the event using produced metrics and the three model vectors; and
comparison of the produced final metric to a threshold to assess whether the event was a positive event or a negative event.

One aspect of this approach is the avoidance of the base-rate fallacy. The base-rate fallacy assumes that a test is "accurate" without considering the relationship (or relative size) between the event probability and the falsing probability. Consider a test having a 99% accuracy. This means that the probability of detecting an on event when there really is an on event is 99%. It also means that detecting an off event when there really is an on event is an event having a 1% probability. Similarly, the probability of detecting an off event when there really is an off event is 99%. It also means that detecting an on event when there really is an off event is 1%. However, if the viewing event has low probability, e.g., the probability of a true on event actually occurring is only 1%, then the probability that the test was accurate when it classifies an event to be a positive event is only 50%.

Now consider a fairly good test having 90% accuracy. The probability of detecting an on event when there really is an on event is 90%. It also means that the probability of detecting an off event when there really is an on event is 10%. Similarly, the probability of detecting an off event when there really is an off event is 90%. It also means that the probability of detecting an on event when there really is an off event is 10%. However, again assuming the viewing event has low probability (e.g., 1% again), then the probability that the test was accurate when it classifies an event to be a positive event is only 9%. Thus, the impact of accuracy of the test is significantly nonlinear.

In the experiment, the collected data set was split into three sets:
60% were used for a training set (for forming the model vectors);
20% were used for a validation set (for model tuning); and
20% were used for a test set (independent of model forming or tuning).

The first pass of the algorithm performed as follows on the test set:
miss percent=between 0% and 5%; and
number of false positives per hour=between 0.3 and 0.6 per hour.

In accordance with an embodiment, the three data sets are used differently to assess performance. The training set is used to associate input features and known event classifications to produce a mapping between input features and prediction metrics. The prediction metric is compared to a threshold to classify an event, and a regularization term is used to tune the algorithm to work with other data sets. The validation data set is used to choose an optimum value for the regularization term lambda. Finally, the test set is used to obtain performance results and to assess independent performance of the model with lambda.

In an embodiment, the event definitions for these models are as follows, although it will be appreciated that other definitions may be used depending upon the underlying physical system:
Accelerometer sample: −10 deg<=tilt<=80 deg and −30 deg<=orientation<=30 deg.
Event=two adjacent accelerometer samples showing a transition from not in-view to in-view. (When there is a transition from not in-view at one sample to in-view at the next sample, those samples are indexed with 0 and 1, respectively. Thus, the 23 samples [−19 . . . 3] indexed for an event reflect 20 before the transition and 3 after the transition. There may be other transitions within the collection of 23 samples that will have been or will be processed in turn.)
The maximum accelerometer magnitude should be less than 4.5 g over the samples from [−19 . . . 3].

The minimum y value over the samples from [−19 . . . 3] should be less than negative 1 g/3. This occurs if the screen has been tipped away from view and away from flat by at least 20 degrees.

Positive event=an event that precedes a button press and that occurs while still in-view is true (marked transition with desired screen on).

Negative event=an event that is not a positive event.

Data Set Used for Model Input, Full Data Set for First Pass Algorithm:

7 users for Turn Over gesture;
~43 million samples @ 25 Hz (about 477.5 hours);
~1000 negative events; and
~150 positive events.

There were two feature sets for the Model's input. The accelerometer only has 248 features for each event.

1 feature: equals constant 1.
1 feature: in-view feature value is 1 if all three samples after transition are in-view, 0 otherwise.
230 features: 23×10 for 230 features.
10 features: 2 angle metrics×5 sample pairs.
The two angle metrics are angle and angle2.
The sample pairs are (−19,1), (−15,1), (−11,1), (−7,1), (−3,1).
The angle is the angle between the two accelerometer points for each pair.
The angle2 is the square of the angle.
6 features: min and max for y,z,m over samples [−19 . . . 3].

While the described examples employ a logistic-regression model, it is possible in theory to use other model types. That said, the inventors found that such other models did not perform as well as the logistic-regression model. Other model types include Linear Regression and Neural Networks. Furthermore, it is possible to use sensors in addition to or other than a 3D accelerometer. For example, it is feasible to use an infrared sensor or a gyroscope. It is also possible to instruct users to employ a different gesture.

Figure 4:
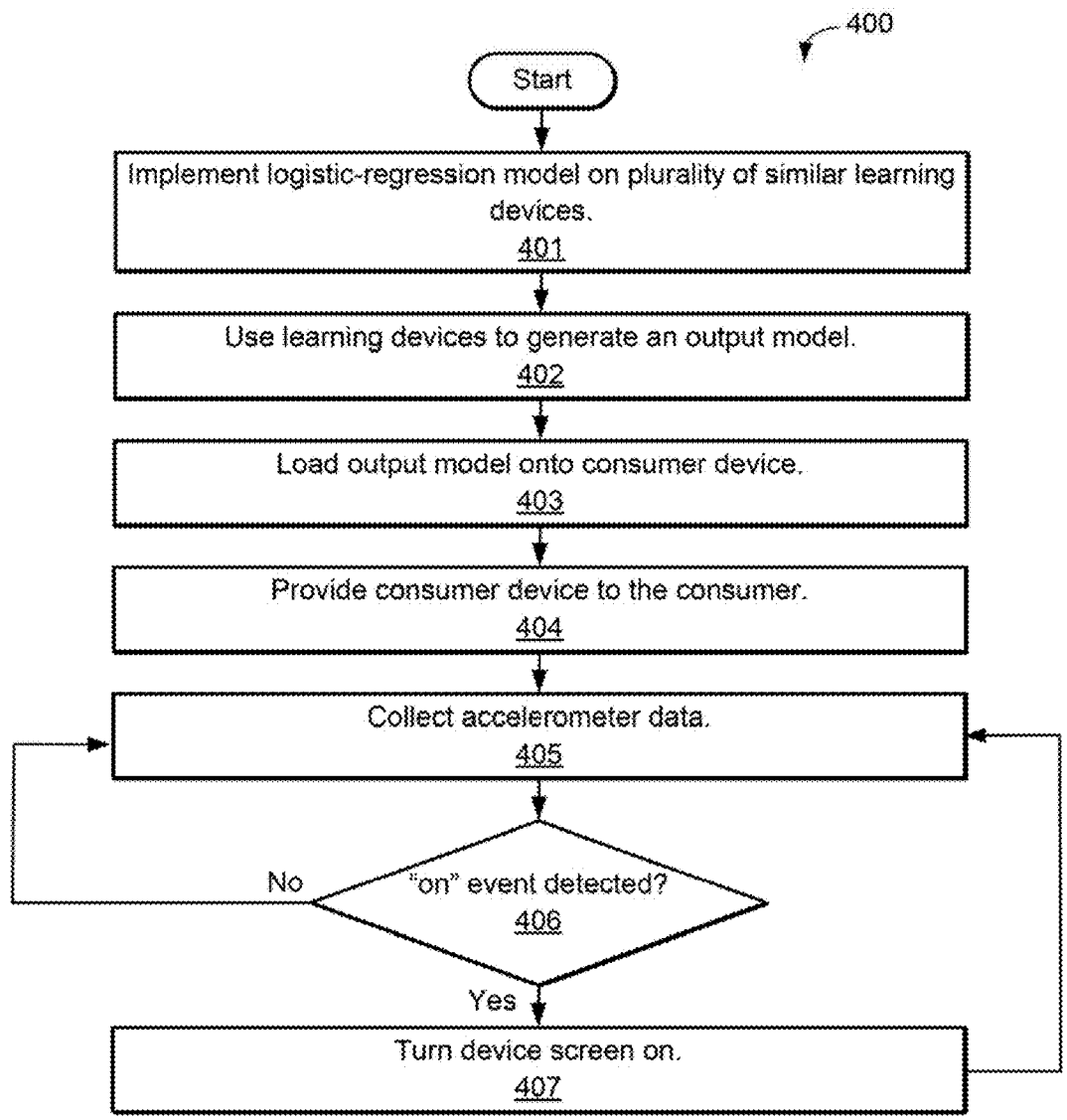
FIG. 4 is a flowchart illustrating a process for deploying a logistic-regression model on a consumer device in accordance with an embodiment of the disclosed principles.

Given the description above, the use of the logistic-regression model to benefit the consumer can now be discussed in greater detail. To this end, FIG. 4 shows a life-cycle process for the deployment and use of machine pre-learned model-based gesture sensing with respect to a wearable watch device.

At stage 401 of the process 400, a logistic-regression model is implemented on a plurality of similar learning devices, that is, devices that are similar to one another and to the consumer device in terms of their response to physical manipulation. The learning devices are used at stage 402 to generate an output model including a vector of metric means, a vector of metric standard deviations, and a vector of metric weights. The details within this step can be understood from reviewing FIG. 3.

The output model is loaded onto the consumer device at stage 403, and at stage 404, the consumer device is provided to the consumer. As the device is worn by the consumer, the processor therein collects accelerometer data at stage 405 and checks for "on" events at stage 406 based on the output model. At stage 407, if an "on" event has been identified, the device screen is turned on. Otherwise the process 400 returns to stage 405.

It will be appreciated that the formed logistic-regression model is applicable to other events definitions. For example, when the user is lying down, a separate event definition can be defined as:

Accelerometer sample: −80 deg<=tilt<=−10 deg and −30 deg<=orientation<=30 deg.
Event=two adjacent accelerometer samples showing a transition from not in-view to in-view.
The maximum accelerometer magnitude should be less than 4.5 g over the samples from [−19 . . . 3].
The minimum tilt value over the samples from [−19 . . . 3] should be greater than 20 degrees.

Another event definition may be implemented when the screen is to turn on when the device is flat and face up. Such a model may be defined as follows:

Accelerometer sample: tilt>=80 deg.
Event=two adjacent accelerometer samples showing a transition from not in-view to in-view.
The maximum accelerometer magnitude should be less than 4.5 g over the samples from [−19 . . . 3].
The minimum away tilt<=−20 over the samples from [−19 . . . 3].
The minimum y<=−3 g/4 over the samples from [−19 . . . 3].
The minimum away tilt is defined as the minimum tilt in the restricted set of tilts over samples [−19 . . . 3] that accompanies a negative y value.

Another event definition may be implemented when the device is worn on the opposite side of the wrist. This event may be defined as:

Accelerometer sample: 10 deg<=tilt<=70 deg and −30 deg<=orientation<=30 deg.
Event=two adjacent accelerometer samples showing a transition from not in-view to in-view.
The maximum accelerometer magnitude should be less than 4.5 g over the samples from [−19 . . . 3].
The minimum tilt value over the samples from [−19 . . . 3] should be less than negative 20 degrees.

The same formed logistic-regression model may be used for faster gestures as well. In an embodiment, this is accomplished by taking the additional step of storing two samples in the history for every new sample. The first one stored is an interpolated sample between two actually sampled points. The second one stored is the true sample. This fills a separate stored history of points indexed [−19 . . . 3] that is filled twice as fast as the normal history which has the same size.

The fast gesture may have specific constraints such as the following:

Accelerometer sample: 10 deg<=tilt<=70 deg and −30 deg<=orientation<=30 deg.
Event=two adjacent accelerometer samples showing a transition from not in-view to in-view.
The maximum accelerometer magnitude should be less than 4.5 g over the samples from [−19 . . . 3].
The minimum y<=−1 g/2 over the samples from [−19 . . . 3].

In view of the many possible embodiments to which the principles of the present discussion may be applied, it should be recognized that the embodiments described herein with respect to the drawing figures are meant to be illustrative only and should not be taken as limiting the scope of the claims. Therefore, the techniques as described herein contemplate all such embodiments as may come within the scope of the following claims and equivalents thereof.

I claim:

1. A method of recognizing a viewing gesture made by a user of a user-wearable device having a three-dimensional ("3D") accelerometer and a viewable display, the method comprising:

providing one or more tester-wearable devices to be worn by testers, each tester-wearable device having at least a 3D accelerometer and a selection element;

collecting accelerometer data and selection-element data as each of the one or more tester-wearable devices is worn, each tester selecting the selection element to signify on events when the display is desired to turn on;

calculating at least one metric based on accelerometer data surrounding each on event and employing the at least one metric as a feature for logistic regression;

generating a potential logistic-regression model describing a relationship between tester motion and tester viewing of the viewable display; and training, validating, and testing the potential logistic-regression model to generate an output model that includes a vector of metric means, a vector of metric standard deviations, and a vector of metric weights.

2. The method of claim 1 wherein the accelerometer data surrounding each on event are biased towards samples prior to the event.

3. The method of claim 1 further comprising loading the output model onto the user device.

4. The method of claim 3 further comprising collecting accelerometer data at the user device and checking for on events based on the output model.

5. The method of claim 4 further comprising powering the viewable display on when an on event is detected.

6. The method of claim 1 wherein calculating at least one metric based on accelerometer data surrounding each on event further comprises identifying as negative events any gestures with respect to which the testers did not select the selection element to signify an on event.

7. The method of claim 1 wherein training, validating, and testing the logistic-regression model to generate an output model comprises employing separate portions of the collected accelerometer data and selection-element data for each of training, validating, and testing.

8. The method of claim 7 wherein the respective portions of the collected accelerometer data and selection-element data for each of training, validating, and testing are about 60%, 20%, and 20%.

9. The method of claim 1 wherein the training, validating, and testing of the logistic-regression model to generate an output model are executed in MATLAB™.

10. A wrist-worn user device comprising:
a viewable display having a powered on mode and a powered off mode;
a three-dimensional accelerometer; and
a controller, the controller being configured to maintain the viewable display in the powered off mode and to sample data from the accelerometer and to detect, based on the sampled accelerometer and a pre-loaded pre-trained logistic-regression model, whether the user intends to view the viewable display, and to change the viewable display to the powered on mode if it is determined that the user intends to view the viewable display.

11. The wrist-worn user device of claim 10 further comprising a strap for affixing the device to the user's wrist.

12. The wrist-worn user device of claim 10 further comprising a power source.

13. The wrist-worn user device of claim 12 wherein the power source is one of a battery and a fuel cell.

14. The wrist-worn user device of claim 10 wherein the viewable display is a touch-screen display.

15. The wrist-worn user device of claim 10 further comprising one or more hardware controls.

16. The wrist-worn user device of claim 15 wherein the one or more hardware controls include one or more of a power control, display-mode control, communication control, and privacy control.

17. The wrist-worn user device of claim 10 wherein the controller is further configured to maintain and cause a display of a time of day.

18. The wrist-worn user device of claim 10 wherein the controller is further configured to maintain and cause a display of a user location.

19. The wrist-worn user device of claim 10 wherein the controller is further configured to provide communication services to the user.

20. A method of providing health data to a user via a wrist-worn user device having a three-dimensional accelerometer and a viewable display in a normally off state, the method comprising:
generating a logistic-regression model describing a relationship between user motion and user viewing of the viewable display;
training, validating, and testing the logistic-regression model via one or more tester devices prior to deployment on the user device to generate an output model;
loading the output model onto the user device; and
while the user device is worn by the user, detecting user health data and detecting user motion, and when the detected user motion indicates, based on the output model, that the user desires to view the viewable display, switching the viewable display to a powered on mode.

21. A method comprising:
configuring, by a wearable computing device of a user, a viewable display to a powered-off mode;
sampling, by the wearable computing device, accelerometer data from a three-dimensional accelerometer included in the wearable computing device;
detecting, based on the accelerometer data and a pre-loaded pre-trained model, that the user intends to view the viewable display; and
responsive to detecting that the user intends to view the viewable display, configuring the viewable display to a powered-on mode.

22. The method of claim 21, wherein the viewable display outputs a graphical user interface in the powered-on mode.

23. The method of claim 22, wherein the graphical user interface includes at least one of a time of day or a user location.

24. The method of claim 21, wherein the viewable display does not output a graphical user interface in the powered-off mode.

25. The method of claim 21, further comprising:
while the wearable computing device is worn by the user, detecting user health data.

26. A non-transitory computer-readable storage medium encoded with instructions that, when executed, cause at least one processor of a wearable computing device of a user to:
configure a viewable display to a powered-off mode;
sample accelerometer data from a three-dimensional accelerometer included in the wearable computing device;
detect, based on the accelerometer data and a pre-loaded pre-trained model, that the user intends to view the viewable display; and
responsive to detecting that the user intends to view the viewable display, configure the viewable display to a powered-on mode.

27. The non-transitory computer-readable storage medium of claim 26, wherein the viewable display outputs a graphical user interface in the powered-on mode.

28. The non-transitory computer-readable storage medium of claim 27, wherein the graphical user interface includes at least one of a time of day or a user location.

29. The non-transitory computer-readable storage medium of claim 26, wherein the viewable display does not output a graphical user interface in the powered-off mode.

\* \* \* \* \*